Dec. 20, 1932. W. F. RAMSEY ET AL Plant Pat. 51
PEACH
Filed June 29, 1932
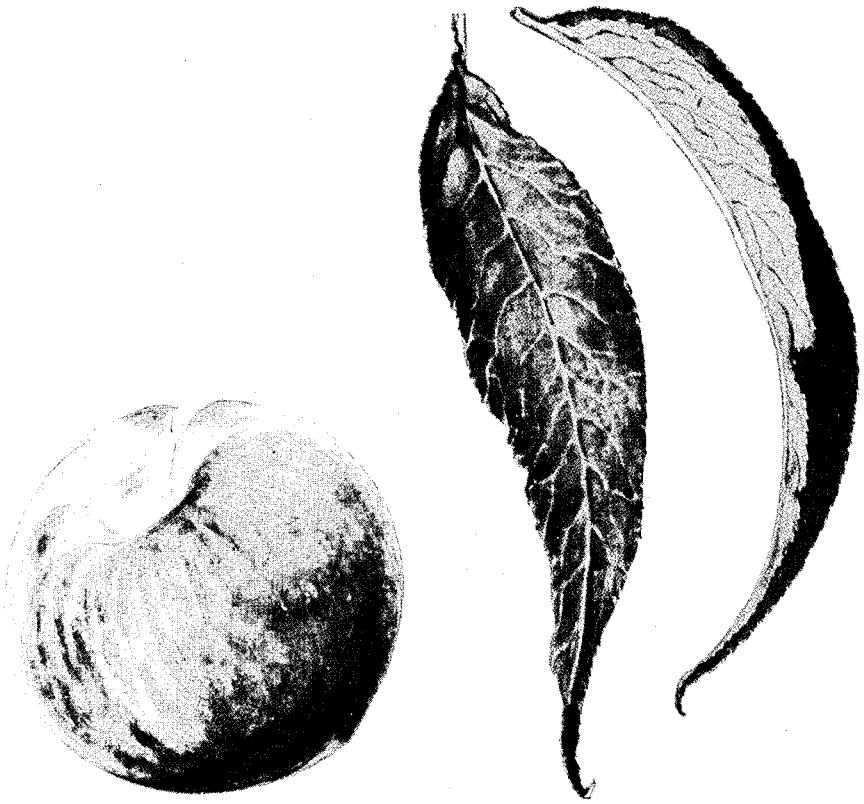
INVENTORS
William F. Ramsey and Andrew T. Gossman
By Orville M. Kile
PLANT PATENT AGENT Patented Dec. 20, 1932

Plant Pat. 51

UNITED STATES PATENT OFFICE

WILLIAM F. RAMSEY, OF OKANOGAN, AND ANDREW T. GOSSMAN, OF WENATCHEE, WASHINGTON; SAID RAMSEY ASSIGNOR TO SAID GOSSMAN

PEACH

Application filed June 29, 1932. Serial No. 620,044.

Our invention relates to improvements in freestone peaches of the type intended for commercial growing and shipping, and in which color, firmness of flesh, a minimum of "fuzz", and ability to stand up under ordinary shipping conditions are important features. The principal object of our invention is to provide a peach of the well-known J. H. Hale type but having much more color, a better flavor, firmer flesh, an almost entire absence of fuzz or pubescence, and superior shipping qualities.

Our new variety was first discovered as a bearing tree on the property of the first named of the joint inventors, in the year 1927. Since that date this new variety has been observed, tested and reproduced by the second named joint inventor. The first peaches of this variety reproduced by top working older trees were grown in 1930 and the first peaches on grafted young trees were harvested in 1931. In all cases the reproduced fruit is identical in general characteristics with the fruit produced on the original tree discovered in 1927, thus establishing the fixed qualities of this new variety.

The accompanying illustration in full color shows an average specimen of the fruit of this new variety ripe and ready to eat, also two leaves.

The following is a detailed description of this new variety:

Fruit, medium size, roundish, regular in shape; stem cavity deep to very deep, wide and moderately furrowed; skin rather thick and almost devoid of the fuzz so commonly found on peaches, in fact this peach is almost as smooth as a nectarine; color, highly colored even when grown on the shady portions of the tree, both bright and deep reds shading into purple at certain points, but with the underlying yellow showing at various points particularly around the stem cavity producing a slightly striped effect; flesh is exceptionally firm, of fine texture, and has a deep yellow color with shades of red around the seed, the latter detaching from the flesh in true freestone manner; flavor can be described as excellent.

This variety ripens at approximately the same time as the J. H. Hale peach but being firmer in flesh it lasts longer and stands shipping better.

The leaves of our new variety are somewhat smaller and more slender than those of the well-known Elberta variety grown under similar conditions of soil and climate. The teeth on the edges of the leaves are much less prominent than on the leaves of either the Elberta or the J. H. Hale grown under similar conditions of soil and climate.

The tree is extremely vigorous in growth, propagates easily, and produces fruit at an early age.

Since this new variety of peach more nearly resembles the J. H. Hale peach than any other known variety, it is desirable particularly to differentiate it from the J. H. Hale. The principal features which we believe clearly distinguish our new variety from the J. H. Hale are as follows:

First, its high coloring, having much more red and purple than the J. H. Hale when grown under similar or identical conditions of soil, climate, pruning fertilization and other factors which might affect color. Ability to produce high coloring even on the shady portions of the tree is particularly notable.

Second, the almost complete absence of fuzz as above described.

Third, its firmer flesh and superior shipping qualities.

Fourth, its better flavor.

Fifth, the much less prominent toothing or serration of the edges of the leaves.

We claim:

A variety of freestone peach of the J. H. Hale type as herein shown and described, characterized particularly by higher coloring, better flavor, almost entire absence of fuzz, firmer flesh and superior shipping qualities.

WILLIAM F. RAMSEY.
ANDREW T. GOSSMAN.